United States Patent [19]

Jensen

[11] Patent Number: 4,923,855
[45] Date of Patent: May 8, 1990

[54] SYNTHETIC GTF CHROMIUM MATERIAL AND PROCESS THEREFOR

[75] Inventor: Ned L. Jensen, Martinez, Calif.

[73] Assignee: The William Seroy Group, Walnut Creek, Calif.

[21] Appl. No.: 186,149

[22] Filed: Apr. 26, 1988

Related U.S. Application Data

[63] Continuation-in-part of Ser. No. 512,111, Jul. 8, 1983.

[51] Int. Cl.$^5$ ................. C07D 213/89; A61K 31/555; A61K 33/24; A61K 35/02
[52] U.S. Cl. ........................................ 514/188; 546/5
[58] Field of Search ............................. 546/5; 514/188

[56] References Cited

PUBLICATIONS

Chatterjee, J. Indian Chem. Soc. 53, 1212 (1976).

Primary Examiner—Mark L. Berch
Attorney, Agent, or Firm—Limbach, Limbach & Sutton

[57] ABSTRACT

A novel product obtained by reacting an alkali metal salt of nicotinic acid with a trivalent chromium salt and having glucose tolerance factor activity, a process for its production and a method for its use, are disclosed.

4 Claims, 1 Drawing Sheet

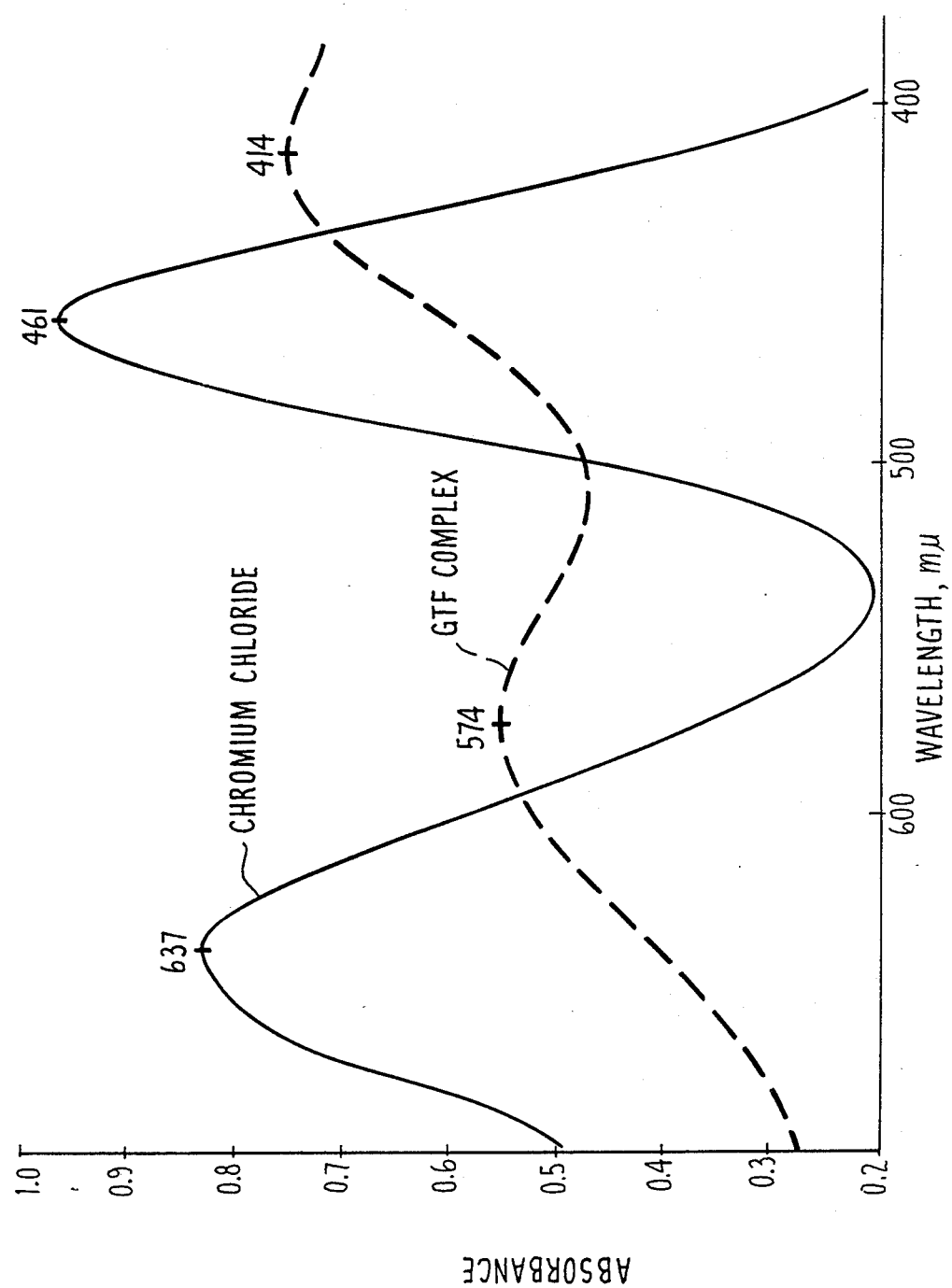

SYNTHETIC GTF CHROMIUM MATERIAL AND PROCESS THEREFOR

RELATED APPLICATION DATA

The present application is a continuation-in-part of commonly-owned and co-pending application serial number 512,111, filed July 8, 1983.

DESCRIPTION

1. Technical Field

The present invention relates generally to glucose metabolism, and more particularly to the production and use of a novel chromium-containing product which has glucose tolerance factor (GTF) activity.

2. Background of the Invention

Although the physiological mechanism is not completely understood, it has been reported that animals placed on a purified, chromium-free diet for several weeks displayed greatly impaired glucose tolerance, i.e. the ability to maintain blood glucose at normal levels. It was found that a diet containing Brewer's yeast would eliminate this impairment and blood glucose levels would return to normal.

The presence of chromium as an organic salt in foods was also found to increase glucose oxidation in humans, particularly when extracts of Brewer's yeast containing chromium were added. In addition, oral administration of such material to a diabetic individual was found to influence the pancreas to produce normal amounts of insulin.

The relationship of chromium content in food and its effects on glucose oxidation activity are discussed, for example, in Toepfer, et al., "Chromium Foods in Relation to Biological Activity," J. Agr. Food. Chem. 21:69 (1973).

These and other findings led to an interest in Brewer's yeast as a source of a naturally occurring glucose tolerance factor (GTF) by early workers in the field of trace mineral research. A discussion of the history of GTF research can be found in McCarthy, et al., "High-Chromium Yeast and Glucose Tolerance Factor," J. Prevention Medicine 2 (1983). Considerable research has been directed towards concentrating the chromium content of Brewer's yeast to a commercially feasible amount. See, for example, U.S. Patent 4,343,905.

Glucose tolerance factor is believed to be a complex of trivalent chromium with two moles of nicotinic acid (niacin) and at least one mole of an amino acid. For example, as suggested by Mertz, et al. in "Present Knowledge of the Role of Chromium," Fed. Proc. 33(11):2275-2280 (1974), it is possible that the structure for natural GTF could be derived from the structure for a tetraaquo-dinicotinato Cr-complex, i.e.,

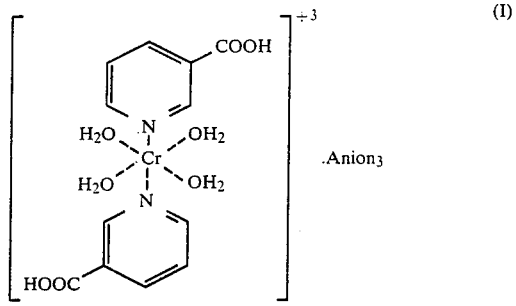

wherein the molecules of water are replaced by amino acid ligands.

Thus, although the exact structure of GTF is not known at this time, one possible structure might be as follows:

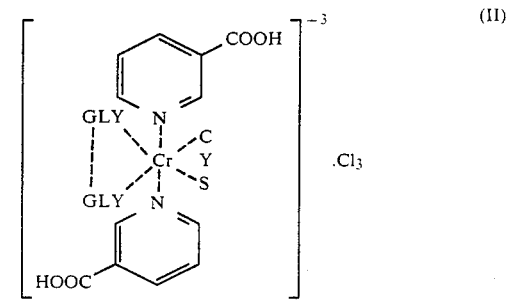

Alternatively, a recent patent application, published as WO 87/03200, reports the isolation and purification from yeast of a compound with GTF activity which is a quinoline derivative having a molecular weight of 174 and a structural formula as follows:

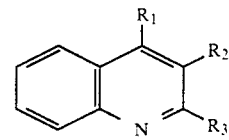

wherein at least one R group is hydrogen and the two non-hydrogen, non-identical R groups are -OCH$_3$ or -NH$_2$. This report includes reference to additional research efforts which cast doubt on the role of chromium and chromium-nicotinic acid-amino acid complexes in yeast GTF activity.

Attempts have also been made to synthesize trace metal complexes which exhibit GTF activity. For example, U.S. Pat. No. 4,242,257 discloses a material exhibiting GTF activity which is obtained by complexing cobalt with nicotinamide in a ratio of 1:2, followed by acidification of the complex and reduction with glutathione. Similarly, the synthesis of chromium-nicotinic acid complexes, which exhibit GTF activity, by refluxing chromium chloride in alcohol for periods of up to about 16 to 24 hours with nicotinic acid and several amino acids has been disclosed. See, for example, Toepfer, et al., "Preparation of ChromiumContaining Material of Glucose Factor Activity from Brewer's Yeast Extracts and by Synthesis", J. Agr. Food Chem. 25(1):162-166 (1977).

There has also been a report of a green chromium complex with pyridine-3-carboxylic acid (nicotinic acid) which was soluble in common organic solvents, including water, acetone, etc. Chatterjee, B., "Donor Properties of Pyridine and Quinoline Carboxylic Acids: Pyridine and Quinoline Carboxylato Complexes of Chromium(III)," J. Indian Chem. Soc. 53:1212–1213 (1976). The report does not disclose any use for the complex.

While the prior art techniques of extracting and/or concentrating chromium GTF from Brewer's yeast have been reasonably successful, the required processing normally is rather complex. This makes the product expensive when used for chromium supplementation of chromium deficient diets or for individuals otherwise requiring chromium supplementation. This problem has not been overcome by synthetically prepared GTF materials because, for the most part, synthetic GTF materials are of limited activity, are formed in relatively poor yields, and/or are highly unstable.

Accordingly, it is an object of the present invention to produce a synthetic GTF material which is stable over extended periods of time.

It is another object of the invention to produce a synthetic GTF chromium complex which can be easily prepared in high yields under relatively mild conditions.

Yet another object of the invention is to produce a non-polar chromium GTF material which would be transported actively at the sites of absorption of nicotinic acid.

Still another object is to provide a chromium GTF material which can be modified easily by an individual's metabolic system to the appropriate isomeric form, or which exhibits biological activity on its own without need for any such modification.

Another object is to prepare a chromium GTF material which is yeast-free and which does not require the use of yeast in its synthesis.

DISCLOSURE OF THE INVENTION

These and other objects and advantages are accomplished in accordance with the present invention by the disclosure of a synthetic chromium-nicotinate GTF material and a process for its production.

In accordance with one aspect of the invention, a chromium-nicotinate GTF material is synthesized under relatively mild conditions using an alkali metal salt of nicotinic acid and a trivalent chromium salt as the starting materials to produce a chromium-nicotinate GTF material in high yields.

In accordance with another aspect of the invention, a chromium-nicotinate GTF material is provided which displays activity comparable to natural glucose tolerance factor, together with a process for its production and a method for its use.

BRIEF DESCRIPTION OF THE DRAWING

The figure is a graphic representation of the UV-V.3 spectra of 10mg/mL chromium chloride and a complex of the present invention.

MODES OF PRACTICING THE INVENTION

In accordance with one aspect of the invention, a process for synthesizing a chromium-nicotinate GTF material is provided by using an alkali metal salt of nicotinic acid and a trivalent chromium salt as the starting materials.

In preparing the chromium-nicotinate GTF material of this invention, a dissociable form of alkali metal, such as an alkali metal hydroxide, and nicotinic acid are first reacted to form the alkali metal salt of nicotinic acid. Thereafter the nicotinic acid salt is reacted with the trivalent chromium salt to form the desired GTF product. Alternatively, the alkali metal salt of nicotinic acid is conveniently obtained from other sources and reacted with the chromium salt to form the desired GTF product.

The reactions normally would be carried out in a polar solvent system, such as an aqueous or alcohol solvent, and would require only mild reaction temperatures, e.g., on the order of from about 5° C. to about 60° C., preferably from about 10° C. to about 40° C. While the stated temperature range is not a rigid requirement, and while temperatures somewhat above or below the stated range could be employed, the added cost of cooling and/or heating the reactants without commensurate benefits in speed or yield is considered to render the use of temperatures outside the stated range less desirable.

If used to prepare the nicotinic acid salt, the dissociable alkali metal may comprise any of a number of compounds containing an alkali metal, including an alkali metal hydroxide, such as sodium hydroxide, potassium hydroxide, lithium hydroxide, or magnesium hydroxide. Alternatively, an alkali metal carbonate or bicarbonate, e.g. containing sodium, potassium, lithium or magnesium, may be used in place of the alkali metal hydroxide.

However, for reasons of economics and ease of handling, it is presently preferred to use sodium hydroxide as the dissociable alkali metal. Sodium hydroxide may be used in the form of food or reagent grade pellets (J. T. Baker Co.) or as a solution. Again, however, to facilitate the preparation of a complex for a food additive, it is preferable to use food grade pellets of sodium hydroxide.

In forming a representative salt of nicotinic acid, the dissociable alkali metal can be added to a solution containing the nicotinic acid and allowed to react without further effort. Such a solution will generally, but not necessarily, be prepared in the same solvent selected for the process of the invention.

The trivalent chromium salts presently preferred for use in the present invention include any readily soluble and pharmaceutically acceptable salts, such as, for example, chromic chloride, chromic sulfate, chromic acetate, and the like, which do not interfere with the formation of the desired chromium GTF material and which do not form toxic by-products. In a presently preferred embodiment, $CrCl_3 \cdot 6H_2O$ (chromium chloride hexahydrate) or $Cr(CH_3COO)_3 \cdot 6H_2O$ (chromium acetate hexahydrate) would be used for the chromium salt.

Solvents which have been found useful in the process of the present invention include polar solvents, such as water and alcohols, typically saturated or unsaturated alkyl chains of from one to 10 carbon atoms, more usually one to six carbon atoms. Such alcohols will have the general formula $$R_1-OH$$

wherein $R_1$ is an organic alkyl group of the form $CH_3(CH_2)_n-$ in either straight chain or branched form and n is a whole number of from 0 to 9. Especially useful solvents have been found to include water and methyl, ethyl, propyl, isopropyl, butyl and isobutyl alcohols, and mixtures thereof.

It will be readily understood, however, that while certain parameters within the following protocols may need to be altered slightly in accordance with known principles, numerous additional polar solvents may be employed in the practice of the present invention. For example, many polar organic solvents, e.g. chlorinated hydrocarbons, ethers, ketones, hydrocarbons and alcohols, either alone or in the presence of water or alcohols, can also find use as solvents in performing the process of the present invention.

The reaction between the chromium salt and the alkali metal salt of nicotinic acid, e.g., sodium nicotinate, takes place quite rapidly and will be evidenced by a distinct color change and subsequent precipitation of the chromium GTF material. For example, when an aqueous reaction medium is employed, the green color imparted to the reaction medium by the chromium chloride salt disappears in a matter of seconds, usually in less than about 60 to 120 seconds, and an intensely purple-colored material precipitates from solution. This precipitated material is the chromium-nicotinate GTF product of the invention, which is believed to contain significant amounts of chromium trinicotinate and, most probably, some chromium dinicotinate mono-chloride, -acetate, or -sulfate, etc., depending upon the anion contained in the chromium salt reactant.

The present invention contemplates a stable synthetic chromium-nicotinate GTF material which has been prepared by reaction between an alkali metal salt of nicotinic acid, such as sodium nicotinate, and a trivalent chromium salt, such as chromium chloride. The crude chromium-nicotinate GTF material comprises at least a substantial portion of a trinicotinic chromium complex (chromium trinicotinate) and the reaction sequence may be represented by the following equations:

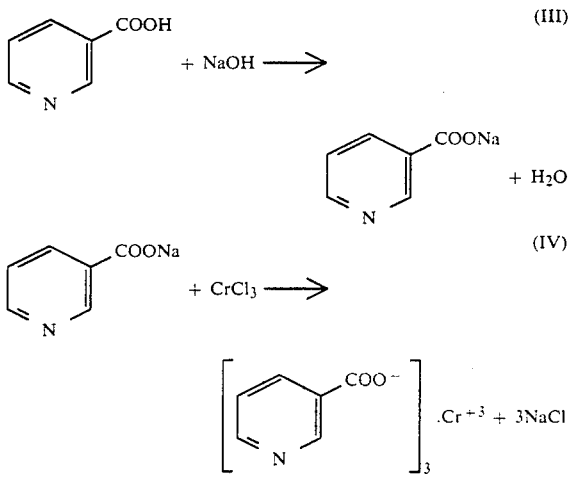

The exact structure of the chromium trinicotinate material is not known, nor is its exact structure critical to the present invention. However, it is believed that the structure of the trinicotinate complex may be illustrated generally as follows:

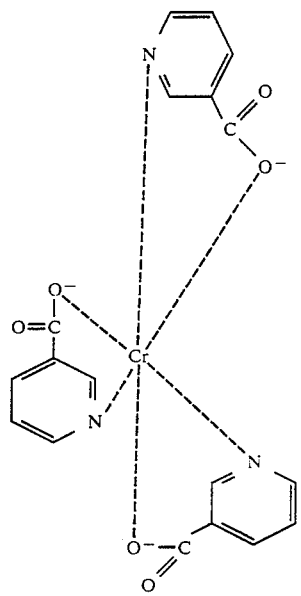

It is likely that the reaction illustrated in equation (IV) does not go to completion and that some dinicotinate complex is formed, thus resulting in a product containing both chromium trinicotinate and chromium dinicotinate mono-anion (e.g., chloride, sulfate or acetate, etc.). It is also possible that some chromium mononicotinate di-anion might be present in the crude reaction product, or that a poly-nuclear species such as dichromium pentanicotinate may be formed. However, it is believed, although not required, that chromium trinicotinate is the predominant reaction product and exhibits the GTF activity in the present chromium-nicotinate GTF material.

Subsequent to its formation, the product of this invention can be dried, for example at temperatures from about 10° C. to about 150° C., preferably from about 20° C. to about 100° C., and at less than 100% relative humidity. In addition, optionally the product can be washed subsequent to its formation in order to remove soluble unreacted compounds which may have become entrapped in the product during the precipitation from solution. Desirable wash solutions would include water and other solvents in which the chromium-nicotinate GTF material is substantially insoluble.

Products of the present invention are shown to have glucose tolerance factor activity in the intact mammal. Furthermore, products of the present invention may demonstrate other effects in vivo, such as increased glucose oxidation levels. Such products shown to have the above recited physiological effects can find use in numerous therapeutical applications such as, e.g., increasing glucose tolerance in chromium deficient patients and potentiating the effect of insulin in diabetics. Thus the products of the invention, and compositions containing them, can find wide use as therapeutic agents.

Thus the present invention also provides compositions containing an effective amount of compounds of the present invention which may, alone, serve to provide the above-recited therapeutic benefits. Such compositions can also be provided together with physiologically tolerable liquid, gel or solid diluents, adjuvants and excipients, as are known in the pharmaceutical art, for example, as described in *Remington's Pharmaceutical Sciences* (16th ed., 1980).

These products and compositions can be administered to mammals for veterinary use, such as with domestic animals, and clinical use in humans in a manner similar to other therapeutic agents. In general, the dosage required for therapeutic efficacy will range from about 0.01 to 1000μg/kg, more usually 0.1 to 1000μg/kg of the host body weight, depending upon such factors as the blood sugar reducing activity of the chromium-nicotinate GTF material, and any particular requirements of the patient. Alternatively, dosages within these ranges can be administered by constant infusion over an extended period of time, usually exceeding 24 hours, until the desired therapeutic benefits have been obtained.

Typically, such compositions are prepared for oral administration, either as liquid solutions or suspensions to be administered independently or as a food supplement. Oral formulations include such normally employed excipients as, for example, pharmaceutical grades of mannitol, lactose, starch, magnesium stearate, sodium saccharin, cellulose, magnesium carbonate, and the like. These compositions contain 10–95% of active ingredient, preferably 25–70%, and take the form of solutions, suspensions, tablets, capsules, sustained release formulations, or powders.

Additional formulations which are suitable for other modes of administration can include suppositories, intranasal aerosols, and, in some cases the compositions are administered parenterally, by injection, for example, either subcutaneously or intravenously. As injectables, the active ingredient is often mixed with diluents or excipients which are physiological tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents, and the like. For suppositories, traditional binders and excipients may include, for example, polyalkylene glycols or triglycerides; such suppositories may be formed from mixtures containing the active ingredient in the range of 0.5–10%, preferably 1–2%.

In addition to the products of the present invention which display GTF activity, products of the present invention can also be employed as intermediates, for example in the further purification of such useful compounds.

EXPERIMENTAL

The following examples serve to illustrate certain preferred embodiments and aspects of the present invention and are not to be construed as limiting the scope thereof.

In the experimental disclosure which follows, all weights are given in grams (g), milligrams (mg) or micrograms (μg), all volumes are given in liters (L) or milliliters (mL) and all wavelengths are given in millimicrons (mμ) unless otherwise indicated.

EXAMPLE 1

In order to illustrate the synthesis of the chromium-nicotinate GTF material of the present invention, a presumptive trinicotinate complex was prepared as follows:

A solution of 3,673 g of nicotinic acid (niacin) USP in 4,540 g distilled water was mixed by stirring. Into this mixture Was added 1,224 g of food grade sodium hydroxide pellets (J. T. Baker Co.) with stirring, thereby forming a solution containing an alkali metal salt of nicotinic acid.

In a separate container, 2,724 g of reagent grade chromium chloride hexahydrate ($CrCl_3 \cdot 6H_2O$) was added to 1,589 g of distilled water and stirred until completely dissolved, to provide a solution containing a trivalent chromium salt.

The chromium chloride solution, which had a green color, was then added slowly to the nicotinic acid salt solution with rapid stirring. The mixture formed an intense purple complex which precipitated from the green chromium solution. The precipitate was collected by filtration and placed on trays to dry.

The intense color change from green to purple and the subsequent precipitation denoted the chemical change of the chromium ion to the complex. This color shift occurred because the atomic orbitals of chromium became occupied, and the wavelength of light absorbed shifted accordingly. The complex precipitated because it had no charge, indicating that the negatively charged nicotinate ions were complexed with the $Cr^+$ ion.

The presence of the complex in the chromium-nicotinate GTF material was further demonstrated by the following analyses:

Chemical Analysis

1. Moisture = 6%–9%
2. Niacin Content = 50%–66%
3. Chromium Content = 8%–10%
4. Sodium Content = 8%–11%
5. Chloride Content = 12%–16%

Elemental Analysis

The content of certain elements in a representative sample of the product showed:

1. Carbon 43.21%
2. Hydrogen 2.77%
3. Chromium 12.9%
4. Nitrogen 8.33%
5. Chloride 3.31%

Polarographic Analysis

A definite shift in the $E-\frac{1}{2}$ was observed. However, good qualitative results were not possible due to the fact that niacin is reduced at about the same voltage range.

UV-V.3 Spectra

As shown in the Figure, two absorbance maxima were observed for chromium chloride in the visible range at 637 mμ and 461 mμ. When the complex was formed, the absorbance maxima shifted to 574 mμ and 414 mμ.

Infrared Spectroscopy

Samples of the chromium-nicotinate GTF material prepared according to Example 1 were washed several times with analytical grade water and dried at 120° C. for three hours. Chromate and nicotinic acid samples were also analyzed by IR spectroscopy. The samples were suspended in a three percent potassium bromide solution and placed between sodium chloride prisms.

As an absorbance control, a chromium chloride blank was made by diluting 158 mg of $CrCl_3 \cdot 6H_2O$ to 100 mL with ethanol to give a kelly green colored solution. The visible light absorbance maxima were 628 mµ and 455 mµ.

The results of the IR analysis showed a single asymmetric stretch peak in the range of 1630 reciprocal wave numbers.

EXAMPLE 2

In order to demonstrate the use of alternative starting materials to form the product of the present invention, 290 mg of nicotinic acid and 249 mg of sodium carbonate were dissolved into 50 mL of water and the pH was adjusted to 7.0 with 0.5M NaOH. Then 158 mg of $CrCl_3 \cdot 6H_2O$ was dissolved in 50 mL of ethanol and the nicotinate mixture was stirred into the chromium chloride solution. A purple complex formed with continued stirring.

The absorbance maxima were measured on a Perkin Elmer 200 ultra-violet visible spectrophotometer and found to be at 568 mµ and 424 mµ. The purple complex precipitate, when dried, formed a crystalline powder substantially insoluble in ethanol or water.

EXAMPLE 3

In order to demonstrate the use of alternative polar solvents in the formation of the product of the present invention, the chromium-nicotinate GTF material was synthesized generally in accordance with the procedure set forth in Example 1, in which the solvent was distilled water, and was also prepared employing ethanol, anhydrous alcohol and methanol as solvents.

In each case, 36.73 g nicotinic acid (niacin) USP was added to 45.40 g of the appropriate solvent until a homogeneous mixture was formed. Next, 17.46mL of NaOH (70% solution) (12.24g NaOH by weight) was added to form the sodium salt of nicotinic acid.

In a separate container, 27.24 g $CrCl_3 \cdot 6H_2O$ (reagent grade, J. T. Baker Chemical Co.) was mixed with 15.9 g of the appropriate solvent and stirred until the $CrCl_3$ was completely dissolved. The chromium chloride solution was then slowly added into the sodium nicotinate solution.

The mixture was then examined for the formation of precipitate. Samples were taken and dried at 100° C. overnight, washed with distilled water, and dried at 100° C. for two hours.

This GTF material was then tested for color. The samples of complex produced in accordance with the present invention in ethanol, anhydrous alcohol, methanol and $H_2O$ each formed purple-blue to purple-grey precipitates, which yielded the same color powder upon drying. The solubility profiles of these complexes are present in Table I.

EXAMPLE 4

In order to demonstrate the importance of the nicotinic acid salt in the formation of a product in accordance with the present invention, 36.73 g of nicotinic acid (niacin) USP was dissolved in 47 mL of anhydrous alcohol. In a separate container, 27.24 g $CrCl_3 \cdot 6H_2O$ was mixed with 16 g of anhydrous alcohol. The chromium chloride solution was slowly mixed with the niacin solution and stirred for two hours at room temperature. The solution did not produce a precipitate.

The product of this example formed a greenish solution which did not precipitate under the test conditions. The dried and washed sample formed a greenish powder.

The samples of complex produced in Examples 1 through 4 were tested for solubility in $H_2O$, methanol, ethanol and anhydrous alcohol. The results of the solubility testing are presented in Table I.

TABLE I

| SOLVENT | EXAMPLE 4 PRODUCT (ALCOHOL) | GTF-ALCOHOL | GTF-$H_2O$ | GTF-METHANOL |
|---|---|---|---|---|
| $H_2O$ | Soluble | Not Sol. | Not Sol. | Not Sol. |
| Methanol | Not Sol. | Not Sol. | Not Sol. | Part. Sol. |
| Ethanol | Part Sol. | Not Sol. | Not Sol. | Not Sol. |
| Anhydrous Alcohol | Part Sol. | Not Sol. | Not Sol. | Not Sol. |

It has been stated that a true GTF material should have the following characteristics:
1. It must improve glucose tolerance;
2. It must be transported across the placenta;
3. The metabolism of adipose tissue must be increased (higher rate of fat and glucose burning); and
4. It must be metabolized differently than chromium chloride and become part of a different biological pool for this element.

Accordingly, samples of the chromium nicotinate reaction product formed in Example 1 were tested to demonstrate their use as a GTF material as outlined

EXAMPLE 5

A synthetic rat food was prepared as a 2.2 g tablet with the following formulation:

| | | | |
|---|---|---|---|
| Vitamin A | 30 IU | Cu | 0.0005 mg |
| D3 | 0.4 IU | Zn | 0.0007 mg |
| Vitamin E | 1.0 IU | Mn | 0.0006 mg |
| Vitamin C | 0.1 mg | Mo | 0.000025 mg |
| Folic | 0.004 mg | K | 5 mg |
| B1 | 0.012 mg | Na | 6 mg |
| B2 | 0.006 mg | Se | 0.00005 mg |
| B3 | 0.02 mg | Inositol | 1 mg |
| B6 | 0.005 mg | Paba | 0.005 mg |
| B12 | 0.000006 mg | V | 0.000025 mg |
| Biotin | 0.0003 mg | EMDEX ®[1] | 900 mg |
| Pantothenic Acid | 0.01 mg | Casein | 900 mg |
| Choline | 0.03 mg | Sunflower Oil | 200 mg |
| Ca | 1.0 mg | SYLOID ®[2] | 20 mg |
| Iodine | 0.0001 mg | Stearic Acid | 20 mg |
| Fe | 0.008 mg | SOLKA-FLOC ®[3] | 200 mg |
| Mg | 0.4 mg | | |

[1]Marketed by Edward Mendell Co., Inc., of Carmel, N.Y., EMDEX ®, also known as Dextrates, is the registered trademark for a highly refined dextrates compound of free-flowing spray-crystallized maltose-dextrose porous spheres. The Chemical Abstract Service registry number is 50-99-7.
[2]Marketed by Davison Chemical Division of W.R. Grace & Co., SYLOID ® micronized, synthetic amorphous silicas are multifunctional food additives.
[3]Marketed by Edward Mendell Co., Inc., SOLKA-FLOC ® is the registered trademark for a family of powdered cellulose products derived from cellulose pulp of the Northern hardwoods (birch, beech, larch and poplar). The Chemical Abstracts Service registry number is 9004-34-6.

Fifteen male albino rats, each weighing between about 180 to 200 g, were placed on a diet of the above synthetic rat food for two weeks. The rats were then divided into three groups of five subjects each. Group was fed only the above synthetic rat food. Group II was fed the synthetic rat food together with 10 ppm of the chromium-nicotinate GTF material of Example 1 added to the drinking water. Group III was fed the synthetic rat food with 10 ppm of chromium as chromium chloride added to the drinking water. This diet regime was maintained for six weeks.

Each subject was weighed every two weeks. The growth rates of the subjects from each group demonstrated that the GTF chromium product had a marked effect on the total body weight and total fat content of the rats. At the end of six weeks on the diet, the subjects were sacrificed, dissected and the organs were assayed for chromium content. The results of the assay for chromium were as presented in Table II.

During dissection, it was noted that the subjects in Groups I and III had large amounts of adipose tissue beneath the skin and laced in the intestines. The effects of the GTF chromium product in preventing the buildup of fatty tissue in Group II subjects were almost immediate.

The growth rates of subjects from Groups I and III were almost parallel, until the toxicity of chromium chloride caused a decrease in the weight of the animals in Group III. The observed toxicity apparently stems from rapid chromium chloride build up in the kidneys.

TABLE II

Body Organ Analysis - Chromium Content

|  | GROUP I | | GROUP II | | GROUP III | |
| --- | --- | --- | --- | --- | --- | --- |
|  | μg/gm | μg/organ | μg/gm | μg/organ | μg/gm | μg/organ |
| Heart | 0.243 | 0.310 | 0.506 | 0.582 | 0.601 | 0.685 |
| Liver | 0.267 | 3.95 | 0.282 | 3.14 | 0.406 | 4.199 |
| Spleen | 0.382 | 0.253 | 0.950 | 0.698 | 0.650 | 0.439 |
| Kidney | 0.184 | 0.341 | 0.443 | 0.652 | 1.136 | 1.823 |
| Muscle | 0.206 | — | 0.179 | — | 0.239 | — |

In addition to the organ analysis, blood was collected from each subject, and the serum was separated from the red blood cells. The serum was assayed for glucose, triglycerides and cholesterol. The results of the serum analysis were as presented in Table III.

TABLE III

Serum Analysis

|  | Glucose mg/DL | Cholesterol mg/DL | Triglycerides mg/DL |
| --- | --- | --- | --- |
| Group I Control | 381 | 53 | 86 |
| Group II GTF | 147 | 48 | 49 |
| Group III CrCl$_3$ | 175 | 52 | 64 |

This example showed that the GTF chromium is metabolized differently than chromium chloride and that it flows to a different biological pool. The GTF chromium also increases the rate of fat metabolism of adipose tissue.

EXAMPLE 6

In order to demonstrate that the chromium-nicotinate GTF material prepared in accordance with Example 1 will be transported across the placenta, 15 timed pregnant albino rats were divided into three groups of five subjects each. These rats were allowed to equilibrate for one week, and were then weighed and placed on the diet regime of Example 5. Group I was the control group and was fed the synthetic rat food of Example 5. Group II was fed the synthetic rat food with the supplementation of 10 ppm of the chromium-nicotinate GTF material of Example 1 added to the drinking water. Group III was fed the synthetic rat food supplemented with 10 ppm chromium as chromium chloride in the drinking water.

At the end of one week, the subjects were weighed, sacrificed, dissected and the organs and fetuses were analyzed as described in Example 5. The results of the analyses were as presented in Tables IV, V and VI.

TABLE IV

Organ Analysis - Chromium Content

|  | GROUP I | | GROUP II | | GROUP III | |
| --- | --- | --- | --- | --- | --- | --- |
|  | μg/gm | μg/organ | μg/gm | μg/organ | μg/gm | μg/organ |
| Heart | 0.38 | 0.372 | 0.37 | 0.368 | 0.34 | 0.347 |
| Liver | 0.42 | 5.67 | 0.29 | 3.48 | 0.30 | 4.034 |
| Muscle | 0.24 | — | 0.28 | — | 0.37 | — |
| Kidney | 0.24 | 0.312 | 0.33 | 0.441 | 0.50 | 0.758 |
| Spleen | 0.45 | 1.478 | 0.47 | 0.289 | 0.63 | 0.378 |
| Placenta | 0.24 | 0.218 | 0.34 | 0.322 | 0.49 | 0.389 |
| Fetus I | 0.17 | 810/fetus | 0.17 | 1,049/fetus | 0.17 | 862/fetus |
| Fetus II | 0.17 | 810/fetus | 0.18 | 1,049/fetus | 0.167 | 862/fetus |

TABLE V

Serum Analysis

|  | Group I | Group II | Group III |
| --- | --- | --- | --- |
| Glucose mg/DL | 307 | 222 | 236 |
| Cholesterol mg/DL | 80 | 61 | 93 |
| Triglycerides mg/DL | 69 | 76 | 104 |

TABLE VI

Weight Analysis

|  | Group I | Group II | Group III |
| --- | --- | --- | --- |
| Mean Initial Weight | 309.8 | 310 | 309.2 |
| Mean Final Weight | 303 | 278 | 296 |
| Percent Change | −2.1% | −10.3 | −4.3 |

This example showed that over the course of one week the chromium-nicotinate GTF material of the present invention was transported across the placenta, achieving a 30% increase in fetal tissue chromium content over the control group and a 21% increase over the chromium chloride group.

It is interesting that the chromium-nicotinate GTF material may not achieve high tissue levels, as it is not concentrated in the tissues and has a very low toxicity. However, it does exhibit biological activity. This indicates that the GTF product acts differently in the body, and enters a different biological pool, from chromium.

The effect of GTF on fat metabolism is dramatic, and total body fat is probably the most sensitive indicator of the activity of GTF chromium. Again, the chromium chloride showed a high retention rate in the kidneys.

EXAMPLE 7

The weight and organ analysis protocols of Example 6 were repeated on a second set of subjects, except that the animals were supplemented for ten days rather than seven, with the results displayed in Tables VII and VIII:

TABLE VII

Organ Analysis - Chromium Content

|  | GROUP I | | GROUP II | | GROUP III | |
| --- | --- | --- | --- | --- | --- | --- |
|  | μg/gm | μg/organ | μg/gm | μg/organ | μg/gm | μg/organ |
| Heart | 0.359 | 0.291 | 0.256 | 0.250 | 0.322 | 0.317 |
| Liver | 0.238 | 2.908 | 0.375 | 4.684 | 0.277 | 3.096 |
| Muscle | 0.262 | — | 0.371 | — | 0.249 | — |
| Kidney | 0.337 | 0.440 | 0.324 | 0.439 | 0.816 | 1.052 |
| Spleen | 0.355 | 0.233 | 0.352 | 0.242 | 0.470 | 0.308 |
| Placenta | 0.324 | 0.252 | 0.364 | 0.232 | 0.338 | 0.231 |
| Fetus | 0.349 | 1.269 | 0.559 | 1.665 | 0.229 | 1.142 |

TABLE VIII

Weight Analysis

|  | Group I | Group II | Group III |
|---|---|---|---|
| Mean Initial Weight | 331 | 343 | 307 |
| Mean Final Weight | 301 | 311 | 262 |
| Percent Change | −9.1% | −9.3% | −14.7% |

This example verified the improved transport of the chromium-nicotinate GTF material of the present invention over chromium chloride and reconfirmed the toxicity of chromium chloride in the kidney.

In the first pregnancy test (Example 6) the reduced level of body fat was demonstrated where body weights were determined after delivery and before dissection; an accurate determination method. In this example, the body weights were determined before dissection, which did not allow for the weight of the fetuses or fluid retention. However, the weight change was found to be approximately the same for Group I and Group II, and both Groups I and II were less than Group III.

It is apparent from the foregoing examples that the chromium-nicotinate GTF material of the present invention exhibits the characteristics of a true GTF complex. Moreover, since the examples illustrate a reduction and/or control of adipose tissue and serum lipid levels in the rats so treated, and since this is a well-known characteristic of prior art GTF compounds, it would be expected that similar effects would be noted on humans treated with the present chromium-nicotinate GTF material. See, for example, Example 2 of U.S. Pat. No. 4,343,905, which is incorporated herein by reference.

When the present invention is used for chromium supplementation in humans the applicable daily dosage for oral administration would depend on the degree of chromium supplementation needed, but may vary from as little as 4 µg to as much as about 500 to 1,000 µg, based on the chromium content of the chromium-nicotinate GTF material. Such supplementation could be made by adding the material to the individual's food or drink, or by administering one or more tablets containing the appropriate levels of the chromium-nicotinate GTF material.

Tablets containing the GTF material of the invention may be prepared, e.g., by dry-mixing 500 mg of EM-DEX®, 5 mg magnesium stearate, 2 mg SYLOID® 74 and 2 mg chromium-nicotinate GTF material in accordance with the present invention. The dry mixture is then pressed into tablets of about 7/16 inch diameter.

A 2 mg portion of the present GTF material provides about 200 µg of chromium, based on present analysis.

The GTF material used is preferably that which has been freed from the salt and water, such as by washing the chromium-nicotinate GTF material prepared in accordance with Example 1 with water and filtering with a Buchner® funnel, using a Whatman® No. 4 filter paper. The filtrate is then rinsed with two more liquid volumes of deionized water and the filter cake dried at 100° C. overnight.

The chromium-nicotinate GTF material may be added to foods and drinks by simply including it into the formulation of the product. For example, it may be added to bread in an amount of about 20 µg chromium per slice at the dough-making stage. This level of supplementation would require approximately 0.1% of the dough to be the chromium-nicotinate GTF material.

When used in treating humans for the purpose of improving glucose tolerance, the dosage would ordinarily be about 500 to 1,000 µg, based on chromium, per day. When used for the treatment of hyperlipidemia, the preferred dosage is from 2 to 4 mg chromium per day, based on the chromium level.

Although the foregoing examples illustrate the preparation and use of particular chromium GTF product, it will be appreciated that the teachings of this application encompass broader and other aspects than recited in the examples. Accordingly, the present invention should be limited only by the scope of the appended claims.

I claim:

1. A method of providing chromium supplementation to mammals, comprising administering in oral dosage form an effective amount of a chromium-nicotinate GTF material obtained by contracting an alkali metal salt of nicotinic acid with a pharmaceutically acceptable trivalent chromium salt.

2. The method of claim 1, wherein the chromium-nicotinate GTF material comprises a mixture of chromium trinicotinate and chromium dinicotinate monochloride.

3. The method of claim 1, wherein the chromium-nicotinate GTF material consists essentially of chromium trinicotinate.

4. A method of providing chromium supplementation to a mammal for the purpose of improving glucose tolerance, comprising administering an effective amount of a chromium-nicotinate GTF material to the mammal, wherein the chromium-nicotinate GTF material is obtained by reacting sodium nicotinate with trivalent chromium chloride.

* * * * *